United States Patent [19]

Segel

[11] Patent Number: 5,374,624
[45] Date of Patent: Dec. 20, 1994

[54] FLUOROCARBON BLOOD SUBSTITUTE

[76] Inventor: Leigh D. Segel, 4215 Almond La., Davis, Calif. 95616

[21] Appl. No.: 105,770

[22] Filed: Aug. 11, 1993

Related U.S. Application Data

[63] Continuation of Ser. No. 741,895, Aug. 8, 1991, abandoned.

[51] Int. Cl.$^5$ .............................................. A61K 31/25
[52] U.S. Cl. ...................................... 514/21; 514/672; 514/673; 514/749; 514/759; 514/756; 514/761
[58] Field of Search ................. 514/21, 672, 761, 756, 514/759, 749, 673

[56] References Cited

U.S. PATENT DOCUMENTS

4,866,096  9/1989  Schweighardt ..................... 514/756
4,895,876  1/1990  Schweighardt ..................... 514/747

OTHER PUBLICATIONS

Saunders, L., "Some Properties of Mixed Sols of Lecithin and Lysolecithin," *J. Pharm. and Pharmacol.*, 9:834–840 (1957).
Jain, et al., "Structure of 1-Acyl Lysophosphatidylcholine and Fatty Acid Complex in Bilayers," *Biochim. et Biophys. Acta*, 642:203–211 (1981).
Hansrani, et al., "The Preparation and Properties of Sterile Intravenious Emulsions," *J. Parenteral Science and Technology.*, 37:145–150 (1983).
Schmolka, I., "Theory of Emulsions," *Federation Proceedings*, 29:1717–1720 (1970).
Flaim, et al., "Characterization and Mechanism of Side-Effects of Imagent PB (highly concentrated fluorocarbon emulsion) in Swine," *Invest. Radio.*, 26:S122–S128 (1991).
Man and Choy, Journal of Modular and Cellular Cardiology, 14 pp. 173–175, 1982, "Lysophosphatidyl Choline Causes Cardiac Arrythmia."
Zvezdina, et al., "Effect of Lysolecithin and Lecithin of Blood Serum on the Sensitivity of Heart to Acetylcholine," *Biochem. Pharmacol.* 27:2793–2801 (1978).
Jain, et al., "Association of lysophosphatidylcholine with fatty acids in aqueous phase to form bilayers," *Nature* 284:486–487 (1980).
Lochner, et al., "Normothermic ischaemic cardiac arrest of the isolated perfused rat heart: effects of trifluorperazine and lysolecithin on mechanical and metabolic recovery," *Basic Res. Cardiol.* 80:363–376 (1985).
Wenzel, D. G. and Innis, J. D., "Arrythmogenic and Antiarrythmic Effects of Lipolytic Factors on Cultured Heart Cells," *Res. Comm. Chem. Pathol. Pharmacol.* 41:383–396 (1983).
Imre, et al., "Membrane Stabilizing Effect of Lysolecithin in Calf Red Blood Cells," *Acta Physiol. Acad. Scien. Hungar. Tomus* 55:113–120 (1980).
Joist, et al., "Inhibition and Potentiation of Platelet Function by Lysolecithin," *Blood* 49:101–112 (1977).
Besterman, E. M. M., and Gillett, M. P. T., "Inhibition of Platelet Aggregation by Lysolecithin," *Atherosclerosis* 14:323–330 (1971).
Clauhan, U. P. S. and Singh, V. N., "Myocardial Phospholipid Metabolism in Alloxan Diabetic Rats," *Life Sci.* 22:1771–1776 (1978).
Kanaho, et al., "Mechanism of Inhibitory Effect of Some Amphiphilic Drugs on Platelet Aggregation Induced by Collagen, Thrombin, or Arachidonic Acid," *Thromb. Res.* 31:817–831 (1983).
Eskalinen, S. and Saukko, P., "The Hypnotic Hemolysis
(List continued on next page.)

*Primary Examiner*—Howard E. Schain
*Assistant Examiner*—P. Lynn Touzeau
*Attorney, Agent, or Firm*—Townsend and Townsend Khourie and Crew

[57] ABSTRACT

The present invention relates to fluorochemical blood substitutes used for preserving mammalian tissue having lysophosphatidyl compounds in non-toxic concentrations. More specifically, the invention relates to aqueous fluorochemical emulsions of a fluorochemical and an emulsifier useful as oxygen delivery agents and methods of preserving tissue in investigational and clinical settings, particularly those settings involving in in vivo transfusion, cardiac and other organ preservation, and in vitro organ perfusion.

31 Claims, No Drawings

OTHER PUBLICATIONS and the Protective Action of Lysophosphatidylcholine," *Biorheol.* 21:363-377 (1984).

Bergmann, et al., "Effects of amphiphiles on erythrocytes, coronary arteries, and perfused hearts," *Am. J. Physiol.* 240:H229-H237 (1981).

Savard, J. D., and Choy, P. C., "Phosphatidyl Choline Formation from Exogeneous Lysophosphatidylcholine in Isolated Hamster Heart," *Biochim. Biophys. Acta* 711:40-48 (1982).

Man, R. Y. K. and Lederman, C. L., "Effect of Reduced Calcium on Lysophosphatidylcholine-Induced Cardiac Arrythmias," *Pharmacol.* 31:11-16 (1985).

McGrath, et al., "Intralipid Induced Haemolysis," *Brit. J. Hematol.* 50:376-378 (1982).

Grimes, J. B. and Abel, R. M., "Acute Hemodynamic Effects of Intravenous Fat Emulsion in Dogs," *J. Parenteral Enteral Nutr.* 3:40-44 (1979).

Fisch, D. and Abel, R. M., "Hemodynamic Effects of Intravenous Fat Emulsions in Patients with Heart Disease," *J. Parenteral Enteral Nutr.* 5:402-405 (1981).

Burnham, et al., "Blood platelet behaviour during infusion of an intralipid-based intravenous feeding mixture," *Postgrad. Med. J.* 58:152-155 (1982).

Ali, et al., "The Acute Effects of Intralipid on Lung Function," *J. Surg. Res.* 38:599-605 (1985).

Lowe, K. C., "Artificial Blood," *British Med. J.* 286:1142-1143 (1983).

Lowe, et al., "Effect of a Perfluorocarbon Emulsion, Fluosol-DA, on Histamine Release from Rat Peritoneal Mast Cells in vitro," *British J. Pharmacol.* 82:276P (1984).

Bollands, A. D. and Lowe, K. C., "Lymphoid Tissue Responses to Perfluorocarbon Emulsion in Mice," *Comp. Biochem. Physiol.* 86C:431-435 (1987).

Lowe, K. C., "Perfluorocarbons as Oxygen Transport Fluids," *Comp. Biochem. Physiol.* 87A:825-838 (1987).

Gillett, M. P. T. and Besterman, E. M. M., "Plasma Concentrations of Lysolecithin and Other Phospholipids in the Healthy Population and in Men Suffering from Atherosclerotic Diseases," *Atherosclerosis* 22:111-124 (1975).

Man, R. Y. K., "Lysophosphatidylcholine-induced Arrythmias and its Accumulation in the Rat Perfused Heart," *Br. J. Pharmacol.* 93:412-416 (1988).

Man, R. Y. K. et al., "The Association of Lysophosphatidylcholine with Isolated Cardiac Myocytes," *Lipids* 25:450-454 (1990).

Sedlis, S. P., et al., "Effects of Lysophosphatidylcholine on Cultured Heart Cells: Correlation of Rate of Uptake and Extent of Accumulation with Cell Injury," *J. Lab. Clin. Med.* 112:745-754, (Dec. 1988).

"Lecithin," in *Approved Drug Products and Legal Requirements*, USPDI, 11th Ed., vol. III, (1991).

Fink, K. L. and Gross, R. W., "Modulation of canine myocardial sarcolemmal membrane fluidity by amphiphilic compounds," *Circulation Research* 55:585-594 (1984).

Corr, P. B. et al., "Amphipathic metabolites and membrane dysfunction in ischemic myocardium," *Circulation Research*, 55:135-154 (1984).

Han, X. and Gross, R. W., "Modulation of cardiac membrane fluidity by amphiphilic compounds and their role in the pathophysiology of myocardial infarction," *Drug and Anesthetic Effects on Membrane Structure and Function*, Aloia, Curtain and Gordon (Eds) N.Y. Wiley-Liss, at pp. 225, 243 (1991).

Jamieson and Greenwalt, Eds., *Blood Substitutes and Plasma Expanders*, A. R. Liss Co., pp. 1-26 (1978).

Cleman, M. et al., "Prevention of ischemia during percutaneous transluminal coronary angioplasty by transcatheter infusion of oxygenated Fluosol DA 20%," *Circulation*, 74(3): 555-562 (1986).

"Lecithin," in USP XXII NF XVII, United States Pharmacopeial Convention, (1990).

FLUOROCARBON BLOOD SUBSTITUTE

This is a continuation of application Ser. No. 07/741,895, filed Aug. 8, 1991, now abandoned.

BACKGROUND OF THE INVENTION

1. Field of the Invention

The present invention relates to fluorochemical blood substitutes used for preserving mammalian tissue having lysophosphatidyl compounds in non-toxic concentrations. More specifically, the invention relates to aqueous fluorochemical emulsions of a fluorochemical and an emulsifier useful as oxygen delivery agents and methods of preserving cardiac tissue in investigational and clinical settings, particularly those settings involving in vivo transfusion, cardiac and other organ preservation, and in vitro organ perfusion.

The need for clinically safe and effective oxygen-carrying media for use as red cell substitutes ("blood substitutes" or "artificial blood") is undisputed. Some of the potential uses for such media include (a) support of organs in vitro prior to transplantation or in vivo during surgery, (b) support of organs or whole animals during experimental investigations, (c) enhancing oxygen delivery to ischemic organs in vivo, (d) enhancing oxygen delivery in poorly vascularized tumors to increase the efficacy of radiation therapy, (e) general transfusion uses, during both routine and emergency situations, (f) diagnostic imaging, and (g) culturing cells.

Blood substitute research is currently focused on hemoglobin-based preparations and fluorochemical emulsions. Fluorochemical emulsions are believed to have major advantages over hemoglobin-based red cell substitutes. Problems associated with hemoglobin preparations include a limited supply of starting material, lack of biological purity, limited ability to deliver oxygen in the presence of erythrocytes, nephrotoxicity, short biological retention times, uncertainty regarding the presence of infectious agents, the large amount of potentially free iron that could propagate oxygen free radical reactions, the presence of unidentified vasoconstrictor contaminants, and hemoglobin inhibition of endothelial derived relaxing factor (EDRF)—mediated vasodilation.

In comparison, fluorochemical emulsions are chemically synthesized, can be made biocompatible, and are free of infectious agents. They dissolve oxygen in direct proportion to inspired oxygen fraction ($FiO_2$) thereby increasing plasma oxygen capacity. Fluorochemical emulsions of several compositions have been shown to deliver oxygen effectively in a variety of settings. A common emulsifying agent is phospholipid from natural sources such as egg yolk. It has been determined that the phospholipids of the prior art fluorochemical emulsions contain lysophosphatidyl compounds in toxic concentrations. The removal of these compounds greatly enhances the preservation ability of the emulsions.

2. Information Disclosure

Schweighardt, U.S. Pat. Nos. 4,895,876 and 4,866,096, describe stable aqueous emulsions of a perfluorochemical, a phospholipid, and a triglyceride of fatty acids which has enhanced stability, diminished particle size and heightened tolerance by biological systems. The patent claims to provide an advance over prior art artificial blood media to provide decreased particle size, increased stability and longer shelf life for an oxygen transport media useful in mammals.

The physiological impact of lysophospholipids has been studied. Fink K. L., and Gross, R. W., 1984, Modulation of canine myocardial sarcolemmal membrane fluidity by amphiphilic compounds, *Circulation Research* 55:585–594, 1984; Corr, P. B. et al., 1984, Amphipathic metabolites and membrane dysfunction in ischemic myocardium, *Circulation Research*, 55:135–154 and Han, X. and Gross, R. W., 1991, Modulation of cardiac membrane fluidity by amphiphilic compounds and their role in the pathophysiology of myocardial infarction, *Drug and Anesthetic Effects on Membrane Structure and Function*, Aloia, Curtain and Gordon (Eds) New York Wiley-Liss, at pages 225–243.

The only fluorochemical emulsion acceptable for clinical use at this time is Fluosol-DA which is described in *Blood Substitutes and Plasma Expanders*, Eds. Jamieson and Greenwalt, A. R. Liss Co., 1978, pages 1–26 (see page 13, Table VI) and in Cleman, M. et al. Prevention of ischemia during percutaneous transluminal coronary angioplasty by transcatheter infusion of oxygenated Fluosol DA 20%, *Circulation*, 74(3): 555–562, 1986.

SUMMARY OF THE INVENTION

This invention provides for aqueous emulsions of a fluorochemical and a phospholipid emulsifier and methods of using such emulsions as oxygen delivery agents. The emulsions provide improved preservation of mammalian organs and tissues over prior art fluorochemical emulsions. The fluorochemical emulsion of the present invention comprises (a) a fluorochemical; and (b) about 0.5 to about 7 percent by weight/volume of a biologically compatible phospholipid emulsifier, the phospholipid emulsifier wherein no greater than about 5 mole percent of the phospholipid consists of lysophosphatidyl compounds. Surprisingly, keeping the amount of lysophosphatidyl compounds below about 5 mole percent yields greater organ (e.g., cardiac) function than over prior art emulsions, when the preservation solutions are otherwise equal in composition.

More specifically, this invention provides for aqueous emulsions of a fluorochemical and an emulsifier producing improved preservation of mammalian organs and tissue, the emulsion comprising: (a) a fluorochemical and (b) greater than about 0.5 weight/volume percent of a biologically compatible phospholipid emulsifier wherein less than about 5 mole percent of the phospholipid therein consists of lysophosphatidyl compounds. By 0.5 weight/vol percent, it is meant that the total weight of the phospholipid is 0.5 grams per 100 milliliters of emulsion including the fluorochemical. It is preferred that the total percent of phospholipid be between about 0.5 and 7 percent weight to volume. This invention further provides for emulsions of the above type where the percent biologically compatible phospholipid is below 0.5% and the emulsion is without Pluronic F-68 TM type surfactant, a polyoxypropylene polyoxyethylene block polymer.

Preferred fluorochemicals are selected from the group consisting of perfluorohydrocarbons and nonperfluorohydrocarbons. Especially preferred fluorochemicals are selected from the group consisting of: fluoroperhydrophenanthrenes having from about 1 to about 24 fluorine atoms; perfluorodecalin; perfluorotrialkylamines; perfluoroctylbromide; perfluoromethyladamatane and perfluoroperhydrophenanthrene.

It is further preferred that the emulsifier contains less than about three and more preferably less than about two mole percent lysophosphatidyl compounds. Zero mole percent lysophosphatidyl compounds is most preferred.

Fluorochemical emulsions in accordance with the present invention preferably have a perfluorochemical average particle diameter of not more than about 0.4 microns and preferably have a diameter ranging from about 0.09 to less than about 0.15 microns.

The emulsions of this invention optionally include an aqueous crystalloid solution and/or various oncotic agents.

The emulsions of this invention are useful for preserving a variety of mammalian organs and tissues and are particularly useful for preserving hearts and cardiac tissue.

This invention further provides for methods of preserving mammalian tissue using fluorochemical emulsions described above. These methods include both in situ situations where the organ or tissues remain in the host mammal and in vitro methods where organs and tissues are removed from the host mammal as in transplant operations.

Further improvements, advantages, embodiments and aspects of the invention will become apparent from the description which follows.

DETAILED DESCRIPTION

1. Definitions.

The following list of definitions is provided to identify to those skilled in the art the precise meaning of the terms.

"Biologically Compatible"—This phrase is meant to include fluorochemical emulsions suitable for clinical applications because of their non-toxic nature. Such emulsions are free of cytotoxic components which can be present in the Pluronic F-68 TM emulsifier used in Fluosol-DA and Fluosol-43. (Pluronic F-68 TM is a polyoxypropylene polyoxyethylene block polymer as described in Federation Proceedings, 34: 1449–1452, 1975.) Although not required, emulsions suitable for in situ or in vivo use preferably have a short biological retention time (half life on the order of 5 to 75 days). Emulsions with longer retention times may be washed out of tissue.

"Cardiac function"—This phrase refers to the stroke work measurement taken at an appropriate heart rate. See Boyle, W. A. and Segel, L. D. Circulation Research 66:710–721, 1990.

"Cardiac tissue"—As used herein, this term is meant to include both whole hearts and cardiac tissue, and is meant to include cardiac tissue from various mammalian species ranging from rat, rabbit, and dog, to human tissue.

"Crystalloid solution"—As used herein the term includes the leading commercial electrolyte solutions, such as Krebs-Henseleit, Burt's, Wicomb's, Bretschneider-HTK, Euro-Collins, St. Thomas II, NIH I, Collins, U. W. solution, Stanford, UCLA/Buckberg solution, and modified versions of the these. The solutions generally have inorganic salts including sodium chloride (NaCl), potassium chloride (KCl), calcium chloride ($CaCl_2$), magnesium chloride ($MgCl_2$), potassium phosphate ($KH_2PO_4$), and sodium bicarbonate ($NaHCO_3$). The concentrations of the components vary depending on the specific use. For example, in cases where the hypothermic preservation of the heart is desired, the potassium and magnesium concentrations are generally kept at a value effective to arrest the heart chemically, while the calcium concentration is kept at a concentration effective to prevent reperfusion tissue damage.

"Emulsifier"—This term is meant to have its usual meaning as a chemical that emulsifies, especially a surface-active agent promoting the formation and stabilization of an emulsion. In the emulsions of the present invention, a fluorochemical is dispersed with an emulsifier in an immiscible liquid (typically water, e.g., Milli-Q Reagent Grade water (Millipore or equivalent), or aqueous crystalloid solution.

"Fluorochemical"—This is a generic term for those fluorinated hydrocarbon and nonhydrocarbon chemicals typically used as oxygen carriers. The various commercial and experimental fluorochemicals now used include the fluorobutylamines, fluorodecalins, fluorotripropylamines, fluoroctylbromides, and fluoroperhydrophenanthrenes. The term "fluorochemical" is meant to include both perfluoronated and nonperfluoronated fluorochemicals. The useful perfluorochemicals can be broken into three groups: (a) perfluoro(alkylcycloalkanes); (b) perfluoro(alkylsaturated heterocyclic compounds); and, (c) perfluoro(tert-amines). Examples of acceptable perfluorochemicals are described in U.S. Pat. Nos. 4,866,096 and 4,895,876, (column 3) which are incorporated herein by reference.

"Lipid"—This term is used to describe the group of natural substances which are soluble in hydrocarbons and insoluble in water. It includes fats, waxes, phosphoglycerides and natural hydrocarbons.

"Lysophosphatidyl compounds"—As used herein, the term means those phospholipids having the fatty acid hydrolyzed off the number 2 carbon atom. The term includes lysophosphatidylcholine (LPC), lysophosphatidylethanolamine (LPE).

"Metabolic Substrates"—This term is meant to include the usual substrates used to enhance the biological compatibility of crystalloid solutions. Examples are natural and synthetic monosaccharides such as glucose.

"Oncotic Agent"—This term refers to proteinaceous and non-proteinaceous compounds which are high molecular weight substances that maintain osmotic pressure over and above that provided by crystalloid solutions. Examples include albumin and hydroxyethyl starch.

"Perfusion"—As used herein, the term means to artificially force a fluid through an organ or tissue by way of blood vessels, typically using an external pump or hydrostatic pressure.

"Pharmaceuticals"—This term refers to chemical compounds used to enhance the biological compatibility of crystalloid solutions with a mammal (i.e., human patient), or to compounds that have a specific physiological, biochemical, or medical effect. Examples include various anesthetics such as lidocaine (reduces $Na^+$ conductance), anti-coagulants such as heparin sodium, antibiotics such as tetracycline, pH buffers such as sodium citrate, and sequestering agents such as disodium EDTA.

"Phospholipid"—Also referred to as phosphoglycerides, are biomolecules which occur widely in plants and animals. Phospholipids have long, nonpolar "tails" and a small, highly polar "head." In aqueous solution, they disperse to form micelles in the same way soaps do. The nonpolar tails close together in the middle of the micelle, leaving the polar heads exposed to aqueous environment. Phospholipids also form bilayers. The natural phospholipids consist primarily of phosphatidyl-choline (PC; also known as lecithin) and phosphatidylethanolamine (PE), with lesser amounts of other phospholipids such as sphingomyelin, lysophosphatidylcholine, lysophosphatidylethanolamine, phosphatidylinositol, etc. For purposes of this document, the term "phospholipid component" shall include the lysophosphatidyl compounds.

"Preservation"—As used herein this term means to keep from decomposition.

"Stable"—This term refers to those fluorochemical emulsions which are not only usable after being frozen but which are usable after being held indefinitely at room temperature (i.e., about 25° C.) or below room temperature but above freezing.

"Tissue"—This term refers to any mammalian material which is living. It includes both individual cells, parts of organs and intact organs.

2. Aqueous emulsions.

The emulsions of this invention have two basic ingredients. They are: (a) a phospholipid emulsifier having a lysophosphatidyl content of less than 5 mole percent of the total phospholipids and (b) a fluorochemical.

Biologically compatible phospholipid emulsifiers used in the compositions and methods of the present invention contain a phospholipid having no greater than about 5 mole percent lysophosphatidyl compounds. Chicken egg yolk is readily available and is of use in the invention. The lysophosphatidyl compounds typically found in egg yolk phospholipids are LPC and LPE. PC and PE typically comprises 73 and 15 percent of a chicken yolk respectively. LPC and LPE comprise about 5.8 and 2.1 percent of the total phospholipids of the chicken yolk. (*Phospholipids Chemistry, Metabolism and Function* Ansell, G. B. and Hawthorne J. N. Elsevier Pub. Co. Amsterdam-London-New York 1964.) Fresh eggs may comprise significantly less lyso-PC. (See U.S. 4,714,571, column 9, lines 24–32).

It has been found that when the lysophosphatidyl compounds in the fluorochemical emulsion are increased above the stated percentages, whole hearts have significantly reduced or no cardiac function after preservation with the fluorochemical emulsion. As the volume percentage of lysophosphatidyl compounds decreases from about 5 molar percent, the cardiac function, contractile and output performance improve significantly.

The purified phospholipids used herein are generally derived from natural sources. They are typically known as lecithin or monoaminomonophosphatide compounds and preferably the fatty acid disubstituted glycerides having choline or ethanolamine esters of phosphoric acid at the third carbon. For example see U.S. Pat. No. 4,866,096 column 4, line 47 through column 5, line 5. Neutral triglycerides may be optionally included in the stable formulation.

The starting material for preparation of the biologically compatible phospholipid emulsifiers suitable for use in the fluorochemical emulsions of the present invention are typically biological materials such as egg yolk and soybean. The starting material can be washed or extracted by a number of known methods to remove extraneous substances such as proteins, which comprise for example approximately one-third of the dry weight of chicken egg yolk.

The lipid portion of a yolk or seed consists primarily of neutral lipids, phospholipids and sterols. These lipids are extracted using one of various known methods, such as chloroform/methanol. Purification of phospholipid components as a class or as individual components is accomplished by chromatography on an absorbent such as alumina or silica gel as described in *Lipid Biochemical Preparations*, Ed. Bergelson L. D. Elsevier North Holland:Amsterdam (1980) and Singh A., *Journal of Lipid Research*, Vol. 31, pp. 1522–1525 (1990) and JP 62,059,287 or by multiple extraction and washing procedures such as those described by Tremblay, et al., U.S. Pat. No. 4,714,571. The phospholipid classes are typically separated using a two-dimensional thin layer chromatography, and the individual classes quantified using a spectrophotometric assay for phosphorus after elution and acid digestion of the separated lipids.

To monitor the purification progress, one can use micro-thin layer chromatography or thin layer chromatography as described by R. C. Aloia and W. Mlekusch (Techniques of Quantitative Analysis of Organ and Membrane Phospholipids and Cholesterol pp. 1–23, 1988. *Methods for Studying Membrane Fluidity*. Aloia, Curtain, Gordon, New York Liss).

Stable aqueous emulsions of a fluorochemical and an emulsifier in accordance with the present invention for producing improved preservation of cardiac tissue generally include one or more of the fluorochemicals defined above. The function of the fluorochemical is to carry oxygen to the cardiac tissue, which depends primarily on the inspired oxygen fraction ($FiO_2$) and upon the concentration of the fluorochemical in the emulsion.

The preferred fluorocarbon for isolated organ perfusion or preservation is perfluoroperhydrophenanthrene. Throughout the range of $PO_2$ values at 12° C., the $O_2$ contents of 10 percent (vol/vol) perfluoroperhydrophenanthrene are twice that of aqueous crystalloid medium. For example, at 12° C. and $PO_2=500$ torr, aqueous crystalloid medium contains about 2.37 ml $O_2$dl, whereas 10 percent vol/vol perfluoroperhydrophenanthrene emulsion contains about 4.73 ml $O_2$dl (i.e., 2.10 ml $O_2$ in the aqueous phase and 2.63 ml in the fluorochemical phase). Particularly good results with the isolated organ preservation experiments have been obtained with perfluoroperhydrophenanthrene.

The concentration of the fluorochemical in the emulsions of the present invention generally ranges from about 10 to about 50 percent vol/vol, preferably from about 35 to about 45 percent vol/vol of the fluorochemical emulsion.

Biologically compatible phospholipid emulsifiers generally comprise from about 0.5 to about 7 percent weight/volume, preferably from about 0.5 to about 4 percent weight/volume of the stable aqueous fluorochemical emulsion. If nontoxic detergents are used to aid emulsification, lower amounts of phospholipids may be used.

The average particle size of fluorochemical particles produced by using these percentages of the emulsifier ranges from a maximum of about 0.4 microns, more preferably ranging from about 0.09 to about 0.15 microns. Particle size is advantageously measured by sedimentation field flow fractionation to confirm the particle size.

The stable aqueous fluorochemical emulsions of the present invention will further comprise an aqueous crystalloid solution. These solutions are available from commercial sources or are easily prepared and have been widely published. Preferred concentrations of inorganic salts for organ preservation by this method are indicated in Table 1. Optional ingredients are also listed in Table 1.

TABLE 1

| Ingredient | Crystalloid Solutions | |
|---|---|---|
| | Broad Range | Preferred Range |
| Electrolytes | | |
| NaCl | 100–150 mM* | 120–130 mM |
| KCl | 5–20 | 10–20 |
| CaCl$_2$ | 0.5–3.0 | 0.7–1.0 |
| MgCl$_2$ | 3.0–10 | 5.0–10 |
| KH$_2$PO$_4$ | 0.5–3.0 | 1.0–3.0 |
| NaHCO$_3$ | 0–25 | 20–25 |
| Optional Ingredients | | |
| Metabolic substrates | | |
| Glucose | 5–15 | 5–10 |
| Mannitol | 50–100 | 60–90 |
| Pharmaceuticals | | |
| Lidocaine | 0.1–0.5 | 0.1–0.3 |
| heparin sodium | 50–150 U/l | 100–120 U/l |
| Oncotic Agents | | |
| Albumin (or hydroxyethyl starch) | 0.2–1.0 wt % | 0.5–0.8 wt % |

*millimolar

Crystalloid solutions for use in the emulsion are described in *J. Thorac. Cardiovasc. Surg.*, 92:238–246 (1986) and in *J. Surg. Res.*, 40:276–284 (1986); *J. Heart Transplant*, 7:456–467 (1988) and Sukehiro, S. et al. *Proc. 3rd World Congr. Open Heart Techn.*, 1989.

Crystalloid salts are commercially available in the electrolyte form from Sigma Chemical Co. of St. Louis., Mo. and Fisher Scientific of Springfield, N.J. The Na+, K+, Ca2+, and Mg2+ concentrations of the fluorochemical emulsions are measured by flame photometry to confirm that dilution factors are correct.

The stable aqueous fluorochemical emulsions of the present invention can further include antioxidants such as Vitamin E and ascorbic acid.

The emulsions of this invention preferably have a viscosity of from about 1.5 to about 17 centipoise and most preferably a viscosity of 1.7 to 2.3 centipoise when measured at 11° using a Cannon-Fenske capillary viscometer (relative to water). Viscosity can be measured using a variety of well known methods. Other apparatus include a Wells-Brookfield cone and plate viscometer at a high shear rate (greater than 100 sec$^{-1}$). When measured at 37° C., the preferred viscosity range is about 1 to about 10 centipoise.

Densities are typically measured gravimetrically. Preferred emulsions have densities which range from about 1.1 grams/ml to about 1.5 grams/ml. Optimum densities are determined empirically using routine methods and are dependent upon on the tissue being preserved and the components of the emulsions.

3. Preparation of the emulsion.

It is preferred that the emulsions be stable. The production of the emulsions involves a multistep procedure which includes the following steps:

(1) The preparation of the aqueous fluorochemical emulsions of the present inventions generally comprises first mixing the fluorochemical and emulsifier to form a first fluorochemical emulsion, typically using microfluidization methods such as those described by Schweighardt, et al., U.S. Pat. No. 4,895,876, incorporated herein by reference in its entirety. In brief, the process consists of:

(a) sterilizing a microfluidization apparatus (Microfluidics, Waltham, MA) with alcohol (ethanol) by passing 250 ml of a 75 vol % alcohol/water solution through the system for about 10 minutes at 10,000 psi back pressure. All components that are removable are steam sterilized at about 120° C. for 15 minutes in an autoclave. All water, fluorochemical and associated glassware are steam sterilized;

(b) combining the fluorochemical and phospholipid emulsifier in the microfluidizer. The phospholipid (itself in an emulsion form) is circulated for five minutes as the pressure is increased from 0 to 14,500 psi. When the pressure remains constant for 30 seconds, one-half of the perfluorochemical volume is added at a rate of 4–5 ml/minute. The resulting partial emulsion is removed from the unit and cooled to 4° C. Processing of the emulsion causes an increase in temperature of 20°–30° C. The temperature must be controlled to cause a stable system to result at high perfluorochemical loadings (>40 wt/vol %) and to avoid denaturing of the emulsifier. At all times the reaction zone, transfer lines and filters are kept at 4° C. with ice/water slush. After the partial emulsion is cooled to 4° C., processing is continued. The remaining 50 volume percent of the perfluorochemical is added at a rate of 6–8 ml/minute with the back pressure at 14,500 psi. When the last volume of perfluorochemical is added, the total emulsion is processed for an additional five minutes. At the stated conditions, the nominal 100 ml volume is processed eight times per minute for a total of 70–80 passes through the Microfluidizer apparatus reaction zone. At all times the fluid being processed is kept below 35° C., preferably below 20° C.

(2) The fluorochemical emulsion can, when needed, either be combined with aqueous electrolyte solutions and metabolic substrates, oncotic agents, pharmaceuticals (e.g., lidocaine, heparin) and/or other additives, or their dry forms thereof, to obtain the desired final concentrations of the desired components. Alternatively, the fluorochemical emulsion can be equilibrated with aqueous solutions of desired nonfluorochemical emulsion components using a process such as equilibrium dialysis.

(3) Equilibration of the aqueous fluorochemical emulsion with a gas mixture having the desired partial pressure of oxygen is the last step. This is achieved through the use of a silastic membrane oxygenator along with the remaining components of a typical heart preservation apparatus which include a microporous filter, an upper reservoir, a lower reservoir, and pump.

4. Clinical use.

The emulsions of this invention have application in clinical scenarios in which oxygen and/or nutrient delivery to organs or parts of the body is desired to help maintain or restore tissue integrity or function.

Clinically, organ preservation prior to transplantation is one important application of this invention. Organs such as the heart, lungs, kidney, liver, pancreas, intestine, etc., are able to be transplanted. By providing needed nutrients to donated organs while they are being preserved, this invention will extend the length of time that the organ can remain viable prior to transplantation. The increased preservation time will permit long-distance transport of organs, better tissue matching of donor and recipient, and an overall better utilization of donated organs worldwide.

Another clinical condition in which this invention has application includes delivery of oxygen to ischemic tissue, a condition which can occur during a traumatic event. For example, "stunned" myocardium resulting from hemorrhagic shock, infarction, etc., or ischemic spinal cord resulting from traumatic injury can be reperfused and resuscitated using the emulsions described herein, thus lessening tissue death. Similarly, this invention could be used to reperfuse organs and tissues that become ischemic during hemorrhagic shock.

Another clinical application of this invention is the delivery of oxygen to tissues during revascularization or thrombolytic therapy procedures. Obstructions, such as atherosclerotic plaques, in blood vessels prevent the free flow of blood to tissue and resulting tissue damage. Methods of revascularization (i.e., reopening or enlarging of the blood vessel lumen to permit blood flow) include balloon angioplasty, atherectomy, and enzymatic methods such as streptokinase administration, for example. During revascularization procedures, tissue damage may be worsened if fluid flow is compromised by the placement of the catheters, or by balloon inflation, needed for the procedure. By infusing emulsion directly to the tissue during revascularization or during administration of thrombolytic agents, oxygen and nutrients can be delivered directly to the area which is at risk and tissue damage can thus be lessened.

Another clinical application of this invention is the delivery of oxygen and/or nutrients to tissues during surgical procedures in which preservation of tissue integrity or function is required. During open-heart surgery, for example, the heart must be metabolically protected so that the tissue does not die while the organ is being operated on. Metabolic protection is achieved by a process called "cardioplegia" in which the heart's metabolic demand is lowered (by cooling the organ) and metabolic support (consisting ideally of oxygen, substrates, and electrolytes) is provided. This invention provides a safe vehicle for cooling the heart and transporting these metabolic nutrients directly to the heart tissue. Similarly, oxygen delivery via transfusion of the emulsion into the circulation would be an application of this invention.

The following examples serve to illustrate specific embodiments of the present invention but do not limit the scope thereof.

EXAMPLES

Example I

Method of Analyzing the Egg Yolk Phospholipid to Determine Percentage of Lyso Compounds All procedures are done under nitrogen and with an anti-oxidant added to the solvents. The lipid is extracted twice, first with chloroform/methanol (2/1) and then with chloroform/methanol (4/1) containing 5% ammonium hydroxide. The extract is filtered, the organic solvent removed by evaporation, and the sample fractionated on Sephadex G-25 column using (chloroform/methanol (19/1).

Phospholipid classes are separated using two-dimensional thin layer chromatography (First dimension: chloroform/methanol/28% aqueous ammonia; 65/25/5) Second dimension: chloroform/acetone/methanol/acetic acid/water; 3/4/1/1/0.5), and then quantified using a spectrophotometric assay for phosphorus after elution and acid digestion of the separated lipids. Phospholipids are identified by comparison to standards. Only those phospholipid emulsifiers having less than about 5 mole percent lysophosphotidyl compounds are used in the examples which follow.

Example II

Preparation of Fluorochemical Emulsion using the Purified Phospholipid from Example I A perfluoroperhydrophenanthrene fluorochemical emulsion is made using purified egg yolk phospholipid from Kabi Pharmacia located in Piscataway, N.J., USA with manufacturing facilities in Clayton, N.C., U.S.A. The commercially prepared lipid is analyzed to ensure that it has less than about 5 mole percent lysophosphatidyl compounds by the method described in Example 1. Suitable pure fluorochemicals are commercially available from Air Products and Chemicals (Allentown, Pa.). The fluorochemical emulsion is prepared using the microfluidization technique described by Schweighardt et al., U.S. Pat. No. 4,895,876. A 6 percent weight-/volume egg yolk phospholipid in water emulsion is made and 35 ml of perfluoroperhydrophenanthrene is added to 65 ml of the water-lipid emulsion to make 100 mls. The perfluorochemical and phospholipid are combined together using the method of Example I.

Example III

Example of a Rat Heart Preservation

The 35 percent (vol/vol) emulsion of the perfluoroperhydrophenanthrene in egg yolk phospholipid of Example II was used to preserve a rat heart. A 40-ml aliquot of the emulsion was equilibrium-dialyzed at 4° C. against a crystalloid solution containing the following: 128 mM NaCl; 15 mM KCl; 0.8 mM $CaCl_2$; 5.2 mM $MgCl_2$; 1.2 mM $KH_2PO_4$; 17 mM $NaHCO_3$; 11 mM glucose; 68 mM mannitol; 0.2 mM lidocaine; 100 U/l heparin sodium, which had been equilibrated with 95% $O_2$/5% $CO_2$ and filtered through a 0.8 micron filter (Millipore). The dialyzed emulsion was brought to a final volume by adding a sufficient quantity of the same crystalloid solution to produce 140 ml of medium containing 10 vol % of perfluoroperhydrophenanthrene. The resulting medium was used as the "Preservation Medium" for a rat heart. The medium contained 4.5 mole percent lysophospatidyl compounds.

The heart was surgically removed from a male 479 g Sprague-Dawley laboratory rat that was anesthetized under pentobarbital sodium anesthesia (63 mg/kg ip) and artificially respirated with room air. The heart was immersed in crystalloid medium ("Cardioplegia Medium") that had the same composition as the Preservation Medium, but without the fluorochemical emulsion component. The heart was perfused with "Cardioplegia Medium" through its coronary arteries for several minutes, gradually cooling the heart to 11° C. The heart was then preserved with the 140 ml "Preservation Medium" for 12 hours at 12° C. Preservation was accomplished by recirculating the "Preservation Medium" continuously through the coronary arteries of the heart at a low pressure (18 mm Hg). The "Preservation Medium" was equilibrated with 95% $O_2$/5% $CO_2$; the pH of the "Preservation Medium" was 7.1, the $PO_2$ was 614 mm Hg, the $PCO_2$ was 43 mm Hg. The $O_2$ and $CO_2$ contents of the emulsions were determined from $PO_2$ and $PCO_2$ values. After 12 hours of preservation, the contractile, pump, and energetic functioning of the heart was tested using an isolated working rat heart apparatus.

An isolated working heart apparatus as described in Boyle, W. A. and Segel, L. D. *Circulation Research* 66:710–721, 1990, tested the function of control (nonpreserved) and preserved hearts at 37° C. and with a workload that was the same as that experienced by rat hearts in vivo. In brief, the left ventricle (LV) was cannulated to obtain LV pressure indices. The pulmonary vein ends were cannulated for perfusate inflow to the left atrium, left ventricle, with exit via the aorta.

The results demonstrated that control, fresh hearts studied in the apparatus immediately upon removal from rats exhibited left ventricular pressure, cardiac output, myocardial oxygen consumption, work, and other functional indices that were the same as those recorded for rat hearts in vivo. More specifically, the pressure, coronary flow, and aortic flow rate data were obtained on-line and stored using a DEC PDP 11/23 minicomputer. Power, work, efficiency, and MVO2 were computed by the minicomputer from the acquired data. The data indicated that the rat heart preserved for 12 hours with the fluorochemical emulsion "Preservation Medium" resumed spontaneous beating immediately upon reperfusion with standard Krebs-Henseleit buffer at 37° C. in the working heart apparatus. The contractile and output performance of the preserved heart was studied for a total of 5 hours. During those 5 hours the preserved heart exhibited functional and energetic indices that were the same as those of control fresh hearts. Thus, the 12-hour preservation with the fluorochemical emulsion medium preserved 100% of the functional capacity of the heart.

Using the above techniques and emulsion, a rabbit heart was preserved for 24 hours with complete recovery of working function.

Example IV

Clinical use of Emulsions

A. Preparation of the Emulsion

The stable aqueous fluorochemical emulsions of the present invention can be combined with solutions of electrolytes (e.g., NaCl, KCl, MgSO$_4$, CaCl$_2$, KH$_2$PO$_4$), metabolic substrates (e.g., glucose), proteinaceous or non-proteinaceous oncotic agents (e.g., albumin, hydroxyethylstarch), pharmaceuticals (e.g., lidocaine, heparin) and/or other additives, or their dry forms thereof, to attain the desired final concentrations of desired components. Alternatively, the fluorochemical emulsion can be equilibrated with solutions of desired nonfluorochemical emulsion components using a process such as equilibrium dialysis. The resulting medium can be equilibrated with a gas mixture having the desired partial pressures (e.g., 95% O$_2$/5% C$_2$, 100% O$_2$), and used to preserve the heart tissue. Preservation and O$_2$ delivery to the tissue can be accomplished by exposing the heart to fluorochemical emulsion in a variety of ways, for example by means of submersion or by perfusion through the coronary bed in a continuous or intermittent fashion.

B. Example of Heart Preservation for Transplantation

For heart or heart-lung preservation, the emulsion is administered either by continuous or intermittent perfusion of the coronary vascular bed via the aortic root or coronary sinus as described in Baldwin, et al. (*Annals of Thoracic Surgery* 43: 670–673, 1987). Briefly, the aorta is cross-clamped and 500 ml of cold (4° C.) emulsion in a cardioplegic solution is administered through the aortic root with appropriate venting. The lungs can also be cooled and flushed with emulsion. The organs are then topically cooled in situ using cold emulsion immediately before excision. After excision the heart can be immersed in and/or perfused with emulsion having the desired composition, prior to transplantation. Similarly, if both heart and lungs are to be preserved, the lungs are cooled and flushed with emulsion and their vasculature perfused with emulsion. Currently, human hearts can be preserved for a maximum of about 4–6 hours, and heart-lung grafts for about 2–4 hours, in both cases using crystalloid (non-fluorochemical emulsion) preservation solutions.

C. Example of Cardioplegia for Clinical Open-Heart Surgery

The emulsion is administered for arrest and protection of the myocardium during cardiac operations. An example of this type of procedure is found in Khuri et al. (*Journal of Thoracic and Cardiovascular Surgery* 95: 442–454, 1988). Briefly, cardiopulmonary bypass is instituted and cardioplegia emulsion, at 4° C., is delivered as a bolus of 500 to 1000 ml into the aortic root after appropriate aortic crossclamping and venting. The emulsion for cardioplegia could contain, for example, 2.5% dextrose, 0.45% sodium chloride., 5 mM sodium bicarbonate, and 20 mM potassium chloride, along with the fluorochemical emulsion. The emulsion is equilibrated with oxygen or oxygen/carbon dioxide to achieve a high PO$_2$ (e.g., 700 mm Hg). Additional doses of cold emulsion are delivered to the left and right coronary ostia, and, in the case of coronary bypass surgeries, the emulsion is also delivered into the ends of the grafts prior to the final anastomoses. The emulsion is delivered every 15-20 min in quantities sufficient to maintain a cool myocardial temperature (e.g., 8°–15° C.).

Alternatively, the emulsion is delivered continuously to the heart at a rate of about 100 ml/min to maintain a cool myocardial temperature. A perfusion pressure of about 55 mm Hg could be used for either the intermittent or continuous administration of emulsion. Appropriate venting of the emulsion from the heart is achieved through either the pulmonary vein or left ventricular apex. Topical cooling with cold emulsion in saline may also be used. After completing the surgical procedure, the aortic clamp can be removed and rewarming of the heart started.

D. Example of Emulsion Use during Angioplasty or Atherectomy

The emulsion is administered during interventional procedures undertaken to restore flow to obstructed or underperfused regions of an organ. Examples of such procedures are angioplasty and atherectomy (*Circulation* 74: 555–562 1986; *Circulation* 81: IV79–IV91, 1990). Regional ischemia can be mitigated during balloon inflation of the percutaneous transluminal coronary angioplasty procedure by delivering oxygenated emulsion at a rate of about 60 ml/min through the central lumen of the dilating balloon catheter. The emulsion is at body temperature (37–38° C.) and contains, for example, physiologically-compatible Ringer's electrolytes and substrates. The emulsion is equilibrated with oxygen or oxygen/carbon dioxide, to give a pH of 7.4 and a PO$_2$ of about 700 mm Hg. A dose of emulsion is infused during each balloon inflation period. A similar procedure could be used during the period of balloon inflation in atherectomy procedures which are used to physically remove obstructions in vessels by knife or laser, for example. Infusion of emulsion directly into the obstructed vessel during enzymatic thrombolytic procedures could be done to provide oxygenation distal to the obstruction as it is lysed. Currently, Fluosol-DA is used during some balloon angioplasty procedures; the emulsion of the present invention would replace Fluosol-DA.

What is claimed is:

1. An aqueous emulsion of a fluorochemical and a biologically compatible phospholipid emulsifier producing improved preservation of mammalian tissue, the emulsion comprising:
   (a) a fluorochemical; and
   (b) a greater than 0.5 percent (wgt/vol) biologically compatible phospholipid emulsifier wherein less than about 5 mole percent of the phospholipid therein consists of lysophosphatidyl compounds.

2. A fluorochemical emulsion in accordance with claim 1 wherein said fluorochemical is selected from the group consisting of perfluorohydrocarbons and nonperfluorohydrocarbons.

3. An emulsion of claim 1 wherein the fluorochemical is selected from the group consisting of:
   a. fluoroperhydrophenanthrenes having from about 1 to about 24 fluorine atoms,
   b. perfluorodecalin,
   c. perfluorotrialkylamines,
   d. perfluorooctylbromide, and
   e. perfluoromethyladamantane.

4. A fluorochemical emulsion of claim 2 wherein said fluorochemical is perfluoroperhydrophenanthrene.

5. A fluorochemical emulsion of claim 1 wherein the phospholipid emulsifier contains less than about two mole percent lysophosphatidyl compounds.

6. A fluorochemical emulsion of claim 1 which further comprises an aqueous crystalloid solution.

7. A fluorochemical emulsion of claim 1 which further comprises a proteinaceous oncotic agent.

8. A fluorochemical emulsion of claim 7 wherein said proteinaceous oncotic agent is albumin.

9. An emulsion of claim 1 wherein the tissue is cardiac tissue.

10. A method of preserving mammalian tissue using fluorochemical emulsions, said method comprising contacting the tissue with an aqueous emulsion of a fluorochemical and a biologically compatible phospholipid emulsifier, the emulsion comprising:
    (a) a fluorochemical; and
    (b) a biologically compatible phospholipid emulsifier wherein less than about 3 mole percent of the phospholipid therein consists of lysophosphatidyl compounds.

11. A method of claim 10 wherein the phospholipid emulsifier contains less than about two mole percent lysophosphatidyl compounds.

12. A method of claim 10 wherein the tissue is contacted with the emulsion while the tissue is in situ.

13. A method of claim 10 wherein the tissue is contacted with the emulsion after being removed from the mammal.

14. A method of claim 10 wherein the tissue is cardiac tissue.

15. A method of claim 10 wherein said fluorochemical is selected from the group consisting of perfluorohydrocarbons and nonperfluorohydrocarbons.

16. A method of claim 10 wherein the fluorochemical is selected from the group consisting of:
    a. fluoroperhydrophenanthrenes having from about 1 to about 24 fluorine atoms,
    b. perfluorodecalin,
    c. perfluorotrialkylamines,
    d. perfluorooctylbromide, and
    e. perfluoromethyladamantane.

17. A method of claim 15 wherein said fluorochemical is perfluoroperhydrophenanthrene.

18. A method of claim 10 wherein the phospholipid emulsifier contains less than about one mole percent lysophosphatidyl compounds.

19. A method of claim 10 which further comprises a proteinaceous oncotic agent.

20. A method of claim 19 wherein said proteinaceous oncotic agent is albumin.

21. A method of claim 10 wherein the emulsion further comprises an aqueous crystalloid emulsion.

22. An aqueous emulsion of a fluorochemical and a biologically compatible phospholipid emulsifier producing improved preservation of mammalian tissue, the emulsion comprising:
    (a) a fluorochemical; and
    (b) a biologically compatible phospholipid emulsifier wherein less than about 5 mole percent of the phospholipid therein consists of lysophosphatidyl compounds with the proviso that the emulsion is without a polyoxypropylene polyoxyethylene block polymer.

23. A fluorochemical emulsion in accordance with claim 22 wherein said fluorochemical is selected from the group consisting of perfluorohydrocarbons and nonperfluorohydrocarbons.

24. A fluorochemical emulsion of claim 23 wherein said fluorochemical is perfluoroperhydrophenanthrene.

25. A fluorochemical emulsion of claim 22 wherein the phospholipid emulsifier contains less than about two mole percent lysophosphatidyl compounds.

26. A fluorochemical emulsion of claim 22 which further includes an aqueous crystalloid solution.

27. A method of preserving mammalian tissue using fluorochemical emulsions, said method comprising contacting the tissue with an aqueous emulsion of a fluorochemical and a biologically compatible phospholipid emulsifier, the emulsion comprising:
    (a) a fluorochemical; and
    (b) a biologically compatible phospholipid emulsifier wherein less than about 5 mole percent of the phospholipid therein consists of lysophosphatidyl compounds with the proviso that the emulsion is without a polyoxypropylene polyoxyethylene block polymer.

28. A method of claim 27 wherein the phospholipid emulsifier contains less than about two mole percent lysophosphatidyl compounds.

29. A method of claim 27 wherein the tissue is contacted with the emulsion while the tissue is in situ.

30. A method of claim 27 wherein the tissue is cardiac tissue.

31. A method of claim 27 wherein said fluorochemical is selected from the group consisting of perfluorohydrocarbons and nonperfluorohydrocarbons.

* * * * *